United States Patent [19]

Simpkins et al.

[11] Patent Number: 5,550,029
[45] Date of Patent: Aug. 27, 1996

[54] METHOD FOR DIAGNOSING ESTROGEN RESPONSIVENESS

[75] Inventors: James W. Simpkins, Gainesville; Jean Bishop, Jacksonville, both of Fla.

[73] Assignee: University of Florida, Gainesville, Fla.

[21] Appl. No.: 303,056

[22] Filed: Sep. 8, 1994

[51] Int. Cl.$^6$ ........................................ C12Q 1/54
[52] U.S. Cl. ........................... 435/14; 436/817; 435/7.21
[58] Field of Search ..................... 435/7.21, 7.8, 435/14; 436/817; 424/1.73; 514/182

[56] References Cited

U.S. PATENT DOCUMENTS 5,176,085  12/1992  Johnson et al. ........................ 435/7.21

FOREIGN PATENT DOCUMENTS

WO94/12782  5/1995  WIPO .

OTHER PUBLICATIONS

Namba, H., Acute Administration of High Doses of Estrogen Increases Glucose Utilization Throughout Brain, Brain Research 291 pp. 391–394.
Renard, "Effects on Carbohydrate Metabolism Before and After Menopause", La Presse Medicale, 22:9, Mar. 3, 1993.
Ahmed–Sorour, H., Role of Ovarian Hormones in the Long–Term Control of Glucose Homeostasis, Hormone Research 13:396–403.
Bishop, J., Role of Estrogens in peripheral and Cerebral Glucose Uilization, Reviews in the Neurosciences, 3(2) pp. 121–137 1992.
Shinkarenko, L., 13C NMR Kinetic Studies of the Rapid Stimulation of Glucose Metabolism by Estrogen in Immature Rat Uterus, NMR in Biomedicine 7 209–217 1994.
1959 Wyke, Electroencephalograph Clin. Neurophysiol. 11:602.
1966 Glowinski et al., J. Neurochem. 13:655–669.
1969 Jaszmann et al., Med. Gynecol. Sociol. 4:268–277.
1970 Oldendorf, Brain Res. 24:37–46.
1971 Oldendorf, Am. J. Physiol. 221:1629–1638.
1974 McKinlay et al., Brit. J. Prev. Soc. Med. 28:108–111.
1974 Merimee et al., N.E.J.M. 191:1275–78.
1977 Utian, Obstet. Gynecol. Survey 32:193–97.
1979 Beatty, Hrom. Behav. 12:112–63.
1980 Ahmed–Sorour et al., Horm. Res. 13:396–403.
1983 Judd, Neuroendocrinology of Aging, J. Meites ed., New York: Plenum Press.
1984 Namba et al., Brain Res. 291:391–394.
1984 Jacquez, Am. J. Physiol. 246:R289–R298.
1985 Puah et al., Endocrinology 117:1366–1374.
1985 Baxter et al., Arch. Gen. Psych. 42:441–47.
1987 Meier et al., Endcrinology 121:1366–1374.
1989 Simpkins et al. in Lomax et al. eds., Thermoregulation: Research and Clinical Applications, Karger Basel, pp. 95–100.
1991 Gasbjerg et al., Biochem. et Biophys. Acta 1062:83–93.
1992 Kostanyan et al., Biochem. Biophys. Acta 1133:301–306.
1992 Bishop et al., Rev. Neurosci. 3:121–137.
1993 Haenngi et al., Maturitas 16:111–122.
1994 Loprinzi et al., N.E.J.M. 331:347–352.

*Primary Examiner*—Ralph J. Gitomer
*Attorney, Agent, or Firm*—Bromberg & Sunstein

[57] ABSTRACT

A method and diagnostic kit is provided for diagnosing responsiveness to a hormone in a human subject that includes determining the amount of glucose utilized by a sample taken from the subject in the presence of the hormone. The sample taken from the subject may include body fluid or body tissue such as blood or skin. The glucose utilized in the test may be labelled for example, with a radioactive label. The diagnostic test may be used to determine responsiveness to estrogen in a human subject prior to treatment with hormone replacement therapy.

12 Claims, 6 Drawing Sheets

METHOD FOR DIAGNOSING ESTROGEN RESPONSIVENESS

TECHNICAL FIELD

Methods for diagnosing responsiveness to estrogen in subjects are disclosed.

BACKGROUND TO THE INVENTION

One of the most prevalent forms of hormone therapy today is that of estrogen replacement therapy in women. Estrogen therapy is prescribed widely not only for the alleviation of menopausal symptoms but also for the prevention of osteoporosis and cardiovascular disease. Furthermore, estrogen may have utility as a therapeutic treatment for chronic neurodegenerative diseases such as Alzheimer's disease.

Estrogen therapy is still very much a "hit-or-miss" treatment. Doses are increased for a patient until symptoms are observed to subside. Some women respond to this approach and others do not. In addition, the treatment protocol may be adversely affected by transient side effects which can be short term (such as nausea or bloating) or long term (such as increased susceptibility to cancer). There is no way to predict, in advance, whether a woman will respond in the long term to estrogen therapy; whether alternative versions of the drug will work better; or whether life-long therapy is for naught.

Numerous studies on the treatment of menopause with estrogen have revealed a dramatic biological variability in response to a common event—the 95% or greater decline in ovarian estradiol ($E_2\beta$) at the menopause. The interpersonal variability in symptoms that is a hallmark of the decline in estrogen levels during menopause is also manifest in the response of individuals to estrogen replacement therapy. Seventy five to 80% of women undergoing the natural menopause, and 95–100% of oophorectomized women experience physiological and/or psychological problems associated with the decline of steroids (Utian (1977), Obstet. Gynecol. Survey 32:193–97). Twenty to 25% of women are unaffected (Haenngi et al. (1993), Maturitas 16:111–122), the remainder of women have symptoms that exhibit a wide variance. These symptoms include hot flushes, perspiration, muscle and joint pain, fatigue, headaches and irritability and vary greatly in both their intensity and frequency (Utian (1977)). Hot flushes, the cardinal sign of the menopause, persist for more than one year in 95% of affected women (Jaszmann et al. (1969), Med. Gynecol. Sociol. 4:268–277; McKinlay et al. (1974), Br. J. Prev. Soc. Med. 28:108–111). Some women experience as few as one flush per month while others have one flush per hour (Jaszman et al. (1969), McKinley et al. (1974)). Menopausal hot flushes can also vary in severity and/or impact from not bothersome to totally incapacitating—in some cases preventing afflicted women from working. Treatment of these menopausal symptoms by estrogen replacement therapy has proved to be effective for some individuals and not for others.

When estrogen replacement therapy is prescribed for additional conditions associated with decline of naturally occurring estrogen including osteoporosis and cardiovascular disease, women may be put on therapy for 20 years or more, not knowing whether the treatment will be effective in preventing these conditions. The uncertainty associated with the outcome of long term estrogen replacement therapy results in unnecessary health care costs; postponement of the use of alternative treatments that might benefit the patient during the time when estrogen therapy is being administered to the unresponsive patient and a certain risk of side effects such as increased susceptibility to breast and endometrial cancers, hypertension and gall bladder disease with no actual benefit to offset the risk for the patient. Furthermore, women who respond well to estrogen may be able to benefit from a reduced dose of estrogen. There are many types of estrogens on the market and many more in research and development. It is possible that one type of estrogen may be better suited to an individual's needs than another. A test that could predict or determine the responsiveness of a patient to estrogen therapy would have utility in therapy planning by reducing the uncertainty now associated with the outcome of longterm estrogen replacement therapy. Such a test would make hormone replacement therapy available to an increased number of women with concomitant overall reduction in morbidity associated with frailty and cardiovascular disease. No test is currently available that measures the responsiveness of an individual to estrogen therapy nor predicts in advance, responsiveness to estrogen therapy.

In some circumstances, estrogen therapy is not recommended regardless of its potential efficacy. For example, in the case of women suffering from breast cancer or for men, hormone replacement therapy using a hormone other than estrogen is desirable for inhibiting hot flushes as well as other symptoms of menopause. An example of such a hormone is megastrol acetate. This hormone which is a progestational agent, has also been found to inhibit hot flushes in androgen deficient males without encountering the adverse side effects seen with estrogen. Other examples of progestational agents are medroxyprogesterone and d-norgestrol. Non-steroidal medications such as dithiocarbomyl hydrazine and clonidine have been found to be partially effective while propanolol, vitamin E, K, mineral supplements, belladonna alkaloids, in combination with mild sedatives, tranquilizers and antidepressants have all been used for relief of hot flushes but their effectiveness has not been critically evaluated (Judd, 1983, Neuroendocrinology of Aging, J. Meites ed., New York: Plenum Press).

As exemplified by estrogen, hormone replacement is a long-term treatment. A method of determining in advance whether hormone treatment could be effective would have utility both in saving medical costs and in avoiding unnecessary adverse side effects associated with the use of these molecules.

Accordingly, a need exists for a method for determining or predicting the responsiveness of individuals to hormone therapy.

SUMMARY OF THE INVENTION

The invention satisfies the above need. A novel method is provided that provides a diagnosis of the ability of an individual to respond to hormone therapy.

A preferred embodiment of this method includes the steps of exposing a sample of the subject to hormone and glucose; measuring the amount of glucose utilized by the sample; and diagnosing hormone responsiveness in the subject based on the amount of glucose utilized by the sample.

In another preferred embodiment, a method for treatment of disorders associated with glucose deprivation in a human subject includes the steps of measuring glucose utilization in a sample from the subject; correlating glucose utilization of the subject with a statistical measure of efficacy of hormone therapy as a function of glucose utilization; and treating the subject with hormone according to the correlation determined by the statistical measure of efficacy.

Another preferred embodiment is a method for evaluating the utility of a novel compound for treating glucose deprivation in a subject, including placing a sample from the subject in a reaction vessel; incubating the sample with the novel compound in the reaction vessel; adding labelled glucose to the reaction vessel; measuring glucose utilization by the sample; and evaluating the utility of the novel compound for treating glucose deprivation.

Another preferred embodiment is a diagnostic kit for measuring responsiveness of a subject to hormone therapy including a reaction vessel for holding a body sample; a hormone preparation for adding to the reaction vessel containing the body sample; a glucose preparation for adding to the reaction vessel containing the body sample; means for measuring a change in glucose utilization by the body sample in the reaction vessel in the presence of glucose and the hormone compared with glucose utilization in the presence of glucose alone.

BRIEF DESCRIPTION OF THE DRAWINGS

These and other features, aspects and advantages of the present invention will become better understood with reference to the following description, appended claims and accompanying drawings where:

DETAILED DESCRIPTION

Figure 1:
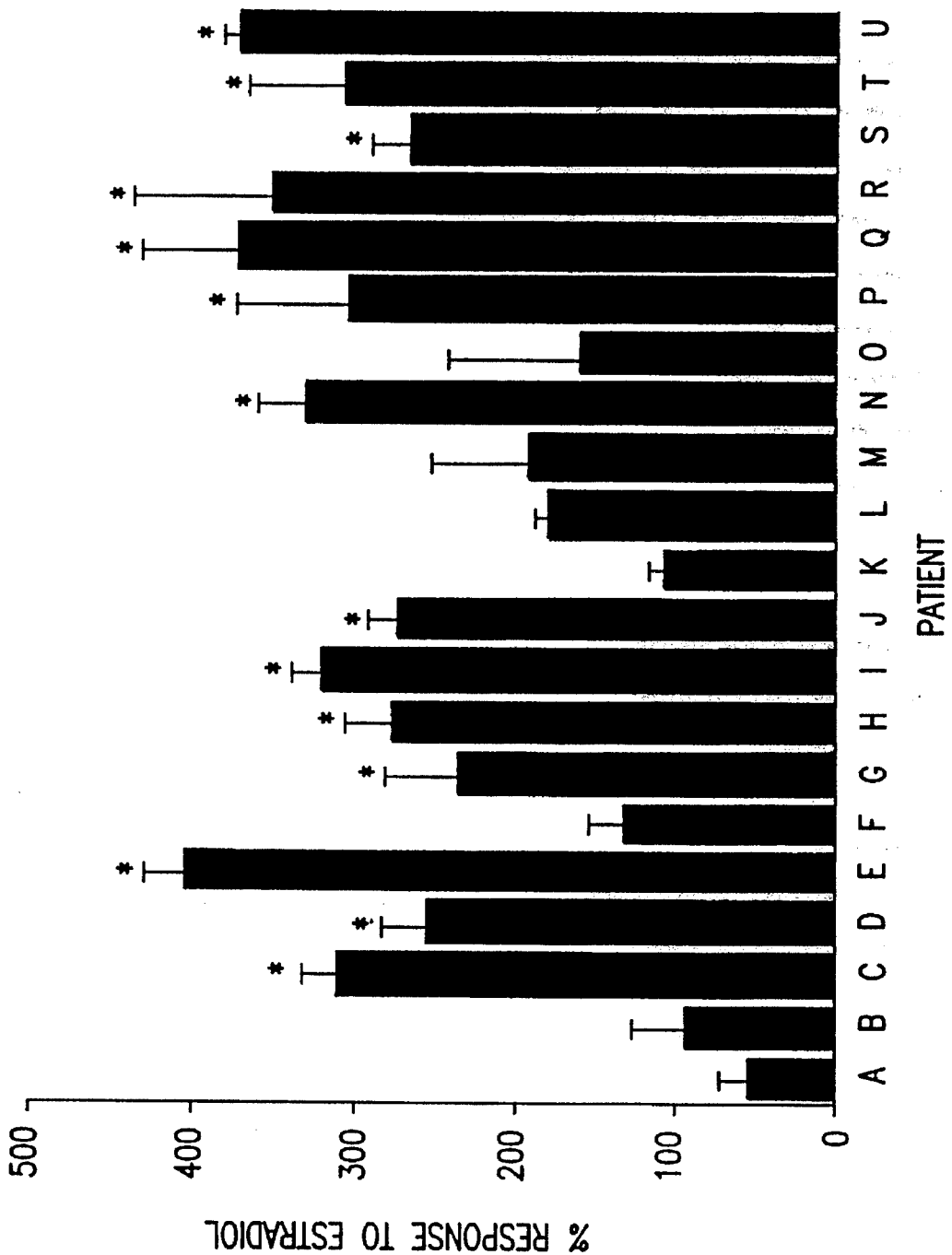
FIG. 1 shows the effects of in vitro exposure of red blood cells (RBCs or erythrocytes) to $E_2\beta$ on $C^{14}$-2-deoxyglucose (2-DG) uptake in the total population (n=21) under study. Data for each patient are expressed as the percent response to $E_2\beta$ exposure (dpms $C^{14}$-2-deoxyglucose uptake in $E_2\beta$ exposed cells divided by the dpms $C^{14}$-2-deoxyglucose uptake in control media-exposed cells multiplied by 100).

The present invention is directed to a method for diagnosing responsiveness of a subject to hormone therapy by measuring the increase in glucose utilization by tissues of the subject.

The term "diagnosing" or "diagnosis" as used in this description and in the claims in connection with hormone therapy responsiveness is defined as the determination or prediction of an effect.

The term "$E_2\beta$" as used in this description and in the claims means 17β-estradiol and is an example of an "estrogen compound" here defined as a form of estrogen including derivative or analogue, either steroidal or non-steroidal that has an effect in this assay.

The term "hormone" as used in this description and in the claims is here defined as an organic compound formed by secretion by an endocrine gland into the circulating fluid; or a synthetic analogue or derivative manufactured in vitro or in vivo. The term "hormone" as used here is further restricted to those compounds capable of causing a change in glucose uptake in vivo or in vitro.

The term "responders" as used in this description and in the claims in connection with hormone responsiveness means those patients who showed a statistically significant response to estrogen exposure.

The term "non-responders" as used in this description and in the claims in connection with hormone responsiveness means those patients who failed to show a statistically significant response to hormone exposure.

The term "subject" refers to humans and other animals.

FIGS. 1–4, the abbreviation "*" as used in this description and in the claims means a statistically significant response to $E_2\beta$ as analyzed by a 2 way t-test for independent samples.

The term "glucose utilization" and "glucose uptake" are here used synonymously.

The discussion below is directed in large part to estrogen. However, the invention is not limited to estrogen but instead may be applied to any hormone that causes a change in glucose uptake.

Hormones and their association with carbohydrate metabolism.

The correlation demonstrated here between glucose utilization and the effectiveness of hormone therapy is novel. Although the involvement of naturally occurring estrogen in the regulation of carbohydrate metabolism has been reported extensively in the prior art (Ahmed-Sorour et al. (1980), Horm. Res. 13:396–403; Bishop et al. (1992), Rev. Neurosci. 3:121–137; Puah et al. (1985), Endocrinology 117:1366–1374), there has been no suggestion in the prior art that an assay that measures glucose utilization might be used to determine responsiveness to estrogen compounds or other hormones administered as a replacement therapy for age-related symptoms, or for treatment of symptoms associated with hypoglycemia. Disorders associated with glucose deprivation include osteoporosis, cardiovascular diseases, neurodegenerative diseases, hypoglycemia, symptoms of menopause and cancer.

Meier et al. (1985), Endocrinology 121:1366–1374; Kostanyan et al. (1992), Biochem. Biophys. Acta 1133:301–306; and Namba et al. (1984), Brain Res. 291:391–394, reported that naturally occurring estrogens increase glucose metabolism in both peripheral tissues (Meier et al. (1987)) and the central nervous system (Kostanyan et al. (1992); Namba et al. (1984)), although the mechanisms of these effects is not well understood. Indeed, the broad influence of estrogen on glucose metabolism may be important in a variety of brain functions, including those with no apparent relationship to reproductive functions" (Beatty (1979). Horm. Behav. 12:112–63). Furthermore, estrogens may have significant therapeutic use in brain disorders associated with a decline in glucose utilization. Decreases in brain glucose utilization of 15–44% have been described during aging (Smith et al. 1982, 5:76–85) and during bipolar depression (Baxter et al. 1985, Arch. Gen. Psych. 42:441–47). Furthermore, a decline in brain glucose utilization may be involved in the menopausal syndrome (Simpkins et al. (1989) in Lomax et al. eds., Thermoregulation: Research and Clinical Applications, Karger Basel, pp. 1312–17), although the extent of decline in glucose metabolism has not been quantified. Our observations in vitro and in vivo demonstrate the positive effect of estrogen treatment on increased glucose utilization where the positive effect includes the prevention of cytotoxic effects (Simpkins et al. application Ser. No. 08/149,175 herein incorporated by reference). Indeed, our observations show that estrogen treatment of humans increase glucose utilization by as much as 230% and suggest that hormones can improve cerebral glucose transport during the menopause and in other disorders involving hypoglycemia.

Glucose utilization plays a role in menopause and hypoglycemia.

We have observed several similarities between symptoms of hypoglycemia (hypoglycemia is defined as low sugar or glucose levels in the blood) and symptoms of estrogen deficiency in postmenopausal women suggesting that both conditions may be caused by, at least in part, a reduction in levels of glucose in the brain giving rise in some circumstances to a state of neuroglucopenia. Menopause has been defined above as the state that arises in aging women when the levels of naturally occurring estrogen fall dramatically. We have correlated the symptoms (in particular, hot flushes) that occur as a result of a decrease in naturally occurring estrogen levels with a decline in blood glucose levels. Seventy-five to eighty percent of menopausal women experience vasomotor symptoms, i.e., hot flushes, during the climacteric. Flushes are frequently accompanied by dizziness, headaches, palpitations and sleep disturbances. For many menopausal women, these symptoms can be effectively treated with estrogen replacement therapy. For a minority of women however, estrogen replacement is not effective. It is proposed that hot flushes and other menopausal sequelae may result from recurrent episodes of hypoglycemia.

Symptoms that arise as a result of hypoglycemia may originate in the brain and include anxiety, sweating, hunger and irritability. Hypoglycemia can result from any of a number of metabolic diseases, pharmacological imbalances, or shock. An example of a pharmacological imbalance is that of insulin overdose in diabetic patients. Insulin overdoses can deplete glucose from circulation and from the central nervous system. Our findings concerning the causes of symptoms of menopause have implications for the treatment of hypoglycemia where a hormone such as estrogen is indicated as a therapeutic agent for this condition. As a first step in developing a treatment for hypoglycemia, the positive effect of estrogen in protecting glioma cells from the cytotoxic effects of hypoglycemia was demonstrated in Example 3. Furthermore, the positive effect of estrogen on cerebral glucose uptake in various regions of the brain was demonstrated in Example 4. Similarly, a diagnostic test suited for determining responsiveness to estrogen in hypoglycemic patients or patients susceptible to hypoglycemia is indicated using the methods described in Example 1.

We have studied the underlying mechanism that links flushing episodes with the uptake of glucose which if inappropriately controlled may lead to hypoglycemia. We have induced flushing episodes in animal models displaying hypoglycemia and neuroglucopenia, and have prevented flushes in animal models and human subjects with acute hyperglycemia. Furthermore, we have shown in animal models that hormone treatment (estrogen) enhances brain glucose uptake, a process that we believe to be mediated by GLUT1 transporters in the blood-brain barrier (Example 4). There exists clinical data that shows sex differences in chronic fasting glucose levels, and suggests a difference in the way hypoglycemia is perceived centrally (Merimee et al. (1974), New England Journal of Medicine 191:1275–78). Wyke (Principles of General Neurology, Amsterdam: Elsevier (1969); and Electroencephalograph Clin. Neurophysiol. (1959) 11:602) has also described a group of patients with relative cerebral hypoglycemia who had normal (i.e., 45–90 mg % glucose) fasting blood glucose levels; raising arterial blood glucose in these individuals to 160 mg % alleviated the symptoms. We have demonstrated that hormones, in particular estrogen play an important role in glucose homeostasis (Example 2). We have provided evidence for a significant role for brain glucose uptake in the manifestation of hot flushes, the cardinal sign of the menopausal syndrome.

Identification of compounds other than estrogen for treating glucose deprivation.

Just as glucose deprivation occurs in both men and women, hot flushes likewise occur in both sexes. For example, men who have undergone androgen deprivation therapy for prostrate cancer commonly experience vasomotor hot flushes.(Loprinzi et al. (1994), New England Journal of Medicine 331:347–352). For both men and women, hormone replacement therapy is used to treat hot flushes. In the case of women, estrogen is the hormone of choice except where women have breast cancer. Treatment of this latter group of women as well as androgen deprived men with a progestational agent such as megastrol acetate, has been shown to be effective in decreasing hot flushes. The effectiveness of megastrol acetate on decreasing hot flushes is indicative of altered glucose uptake in vivo and also demonstrates that additional hormones or derivatives have similar therapeutic effects to that of estrogen.

An assay such as described in an embodiment of the invention can provide for the first time, a means of evaluating the suitability of novel compounds for the treatment of glucose deprivation.

Diagnostic test.

It has been calculated that plasma carries approximately 61% of glucose and erythrocytes carry the remaining 39% (Jacquez (1984), Am. J. Physiol. 246:R289–R298). Red blood cells (RBCs) thus transfer a significant proportion of blood glucose and provide an extra reservoir, or buffer, for the plasma glucose levels as glucose is transported and utilized by tissues. It is suggested here that not only is erythrocyte glucose an important factor in the regulation of blood glucose levels but that human population subgroups might vary in their sensitivity to hormones involved in its regulation.

We have shown that 75% of female subjects exhibit enhancement of RBC glucose Uptake in an in vitro assay performed in the presence of estrogen (FIG. 1). This RBC response may be mediated by the GLUT1 transporter, the same membrane protein present in the endothelial cells of the blood-brain barrier as well as in erythrocytes, glial cells, uterine tissue, and most tumor cells.

The diagnostic test proposed here, known as the "Hormone Responsiveness Diagnostic" can be used to determine the utility of hormone therapy for individuals. Based on such diagnoses, optimal therapies can be designed on a patient by patient basis. The Hormone Response Diagnostic Test described in a preferred embodiment, utilizes RBC glucose uptake in vitro as an indicator of hormone responsiveness in vivo.

In a preferred embodiment, estrogen responsiveness is measured using an assay for glucose utilization. This assay may utilize radioactively labelled glucose (as in Examples 1–2)although it would be equally feasible to use glucose tagged with a non-radioactive marker including fluorescent or luminescent molecules either directly or indirectly, the latter involving for example, antibodies or molecules that are recognizable by specific antibodies. It may also be possible rather than monitoring directly glucose uptake to monitor a surrogate marker like an RNA whose activity or abundance is changed, or a protein whose activity is changed, in response to glucose uptake.

Approaches to measuring glucose utilization may include the use of scintillation counters, fluorescence or chemiluminescence detectors, chromatography papers containing colored molecule which become visible in the presence of threshold amounts of glucose uptake by the sample, gel based chromatography that may provide a measure of nucleic acid marker, immunological techniques and spectophotometers for recording optical density and other means well known in the art for detecting a marker of the types described above. Furthermore, it may be desirable to measure the activity or the concentration of the GLUT transporter in the RBC membrane as an indirect measure of enhanced glucose uptake. Suitable approaches to the measurement of GLUT transporter may include Western Blots of RBC ghosts.

In embodiments of the invention, separation of the sample from the reactants may be accomplished by methods well known in the art including centrifugation, ultrafiltration, immunological techniques including immune precipitation and chromatography.

Although RBCs are used in the diagnostic tests described herein, other samples of a human subject such as body fluids including whole blood or urine or body tissue including white blood cells, and skin, may be used to measure glucose utilization as an indicator of efficacy of a hormone therapy.

In another preferred embodiment, responsiveness to progestational agents such as megastrol acetate, medroxyprogesterone and d-norgestrol, non-steroidal medications such as dithiocarbomyl hydrazine and clonidine, propanolol, or vitamin E, K, mineral supplements, belladonna alkaloids, in combination with mild sedatives, tranquilizers and antidepressants can be measured using an assay for glucose utilization as described above.

This present study demonstrates the following: firstly that acute hormone exposure has an effect on glucose uptake by red blood cells and secondly, that this effect can be monitored in vitro and response to hormone can be correlated to other in vivo parameters.

In Examples 1A and 1B, human patients are analyzed for their responsiveness to hormone by determining levels of glucose utilization. These studies use similar experimental protocols to measure glucose utilization but in addition, examine various differing parameters.

EXAMPLES 1A AND 1B

Determination Of Estrogen Responsiveness in Human Subjects by Measuring Glucose Uptake in RBCs.

Example 1A

Materials and Methods

Collection of blood samples for in vitro diagnostic test.

Freshly drawn heparinized samples (2.5 ml blood with 250 units heparin sodium in sterile water; sodium heparin from Elkins-Sinn, Inc., Cherry Hill, N.J.) were placed in 15 ml Corning polypropylene sterile centrifuge tubes with plugged seal caps (Corning Glass Works, Corning, N.Y.). The cells were immediately isolated from the plasma by centrifugation at 1500 rpms (416×Gs) for 20 minutes at 4° C. After the first centrifugation, the buffy coat containing the white blood cells was removed and the serum samples were frozen at −90° C. for estradiol ($E_2\beta$) assay. Also at this time, an aliquot of serum was assayed for glucose and lactate (YSI Stat 2300 Analyzer, YSI, Inc., Yellow Springs, Ohio). The RBC fraction was washed three times and precipitated by centrifugation at 4° C. and 1500 rpm for 20 minutes in between washes. This paradigm has been demonstrated to reduce intracellular levels of glucose to very low levels (Gasbjerg et al. (1990), Biochem. et Biophys. Acta 1062:83–93). The wash buffer was 37° C. Krebs Ringer Phosphate (glucose free) consisting of 136 mM NaCl, 5 mM $NaH_2PO_4$, 1 mM $CaCl_2$, 1.25 mM $MgSO_4$, 4.7 mM KCl and supplemented with 200 mM 1-glutamine, pH 7.4. Finally, the cells were counted on a hemacytometer and resuspended in one of the following buffers to obtain a concentration of 5 million cells/ml:

(1) Krebs' Ringer Phosphate (controls); or (2) Krebs' Ringer Phosphate+hormone (estradiol ($E_2\beta$) (544 pg/ml)).

Assay for glucose utilization in the presence and absence of estrogen.

0.2 ml (approximately 1 million cells) aliquots were placed in separate wells (reaction chambers) of Falcon 24 well culture plates (reaction vessel). After 4 hr of incubation in one of the above buffers (1) or (2) at 37° C., the buffer was aspirated, cells were washed once with the buffer and the cells were either pulsed with 100 µl $C^{14}$-2-deoxyglucose in Krebs Ringer Phosphate (specific activity 53.1 mCi/mmol, New England Nuclear, Boston, Mass.) or incubated for 5 or 20 minutes in the presence of $C^{14}$-2-DG before removing the labelled glucose marker.

Cells were then washed with 100 µl of Krebs Ringer Phosphate, vortexed, and centrifuged twice. Cells were solubilized with 2×250 µl aliqouts of 1% SDS (sodium dodecyl sulfate, Sigma Chemical Company, St. Louis, Mo.) in double deionized water. Five ml of Formula 989 scintillation cocktail was added. The samples were vortexed and then were counted on a Beckman 5000 TD scintillation counter.

Selection of human subjects.

The University of Florida's Institutional Review Board approved all studies and protocols which use human subjects. Twenty-one healthy men and women volunteered to participate (age range 22–64 years). Some individuals, where noted, consented for repeat sampling. In this study, subjects were recruited at random in order to assess person to person variability and the effect of age and sex on the assay. All subjects were bled late morning (between 10:00 and 11:00 a.m.) except for the study where 2 volunteers were bled at 10:00 a.m. and then at 2:00 p.m. No restrictions were placed on diet or activity prior to the sampling time. The characteristics of the population are defined in Table I. Prior to or immediately following the sampling time, patients answered a thirteen question survey describing information about their individual health and lifestyle. Questions ranged from general (sex, age, height weight) to more specific (medications, menstrual history, meal status).

Results

Table I shows the characteristics of the patient population used in the present study. Twelve women (age±SEM=39.6±3 years) and 9 men (age±SEM=36.8±3.4 years) were asked to complete a questionnaire and be subjected to the withdrawal of a blood sample for the subsequent analysis of $C^{14}$-2-deoxyglucose ($C^{14}$-2-DG) uptake into their erythrocytes (RBCs). All subjects were healthy at the time of the blood sampling, but were not controlled in any other way. That is they were not purposefully fasted or asked to refrain from smoking or any other activity prior to the sampling.

In a preliminary evaluation, RBCs from a 45 year old male subject were processed as described above and then were exposed to $C^{14}$-2-DG. At 5 or 20 minutes the experiment was terminated and the amount of $C^{14}$-2-DG trapped in the RBCs was determined. This preliminary experiment showed that the uptake of the $C^{14}$-2-DG was rapid and progressed over the time studied. Further, the small variance observed in the estimate of the mean value of 3 to 5 replicates of cells from this subject indicates that the method was accurate and consistent. As such, we expanded our observations to other patients.

FIG. 1 depicts the typical values obtained from RBCs when they are exposed in vitro to estradiol ($E_2\beta$) or to control media (controls). Of the 21 patients examined, 14 showed a significant response to in vitro exposure to $E_2\beta$, while 7 patients failed to respond to the estrogen.

For the total population, the female subjects and the male subjects, the magnitude of the increase in $C^{14}$-2-DG uptake response to $E_2\beta$ was 127%, 194% and 56%, respectively (Tables II, III).

Figure 2:
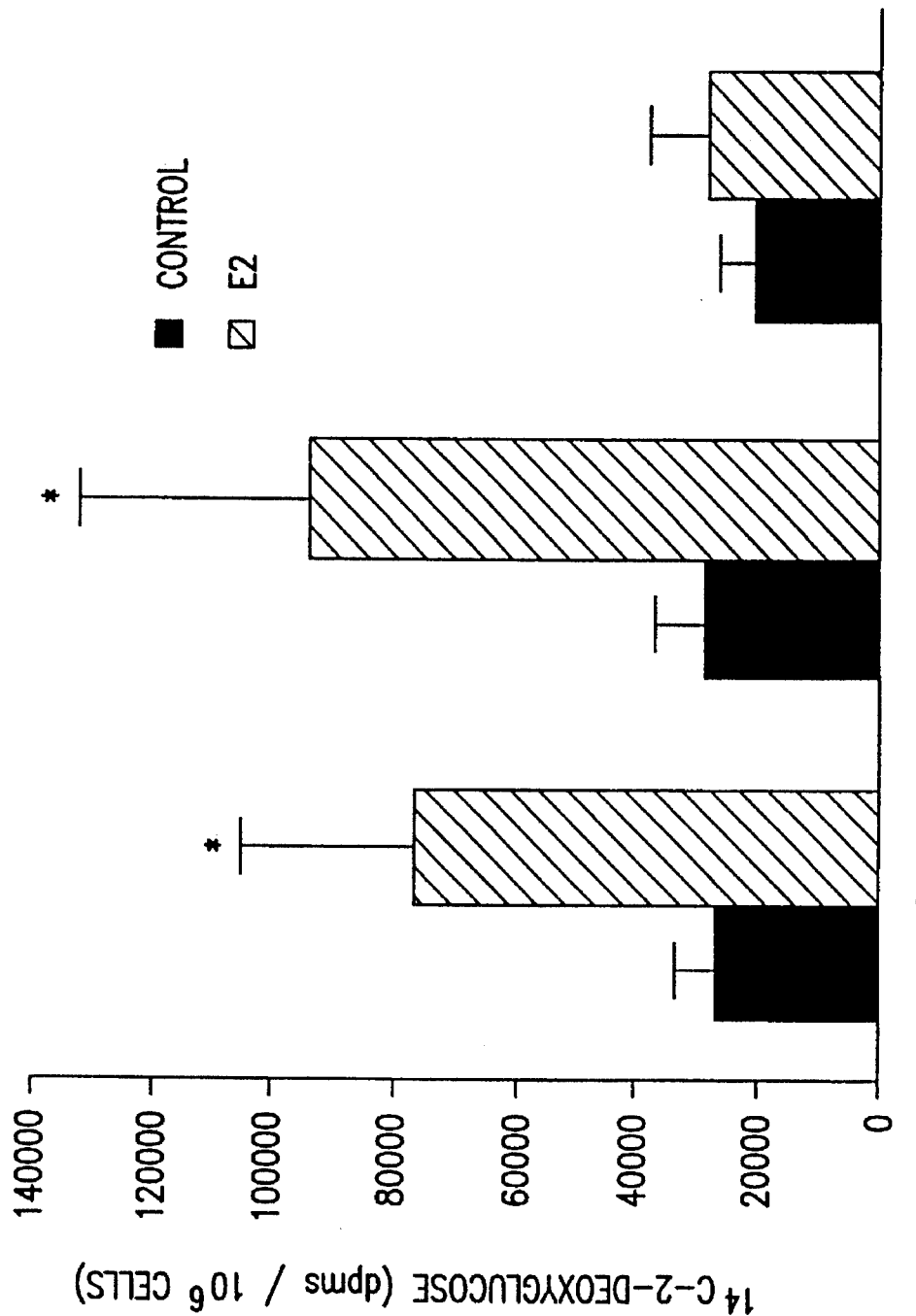
FIG. 2 shows effects of in vitro exposure of erythrocytes to $E_2\beta$ on $C^{14}$-2-deoxyglucose uptake in the female population (n=12 patients) under study. Depicted are dpm/$10^6$ cells in replicates of 3–5 samples of cells treated with the control media (controls, solid bars) or (544 pg/ml, hatch bars) for 4 hours.
Figure 3:
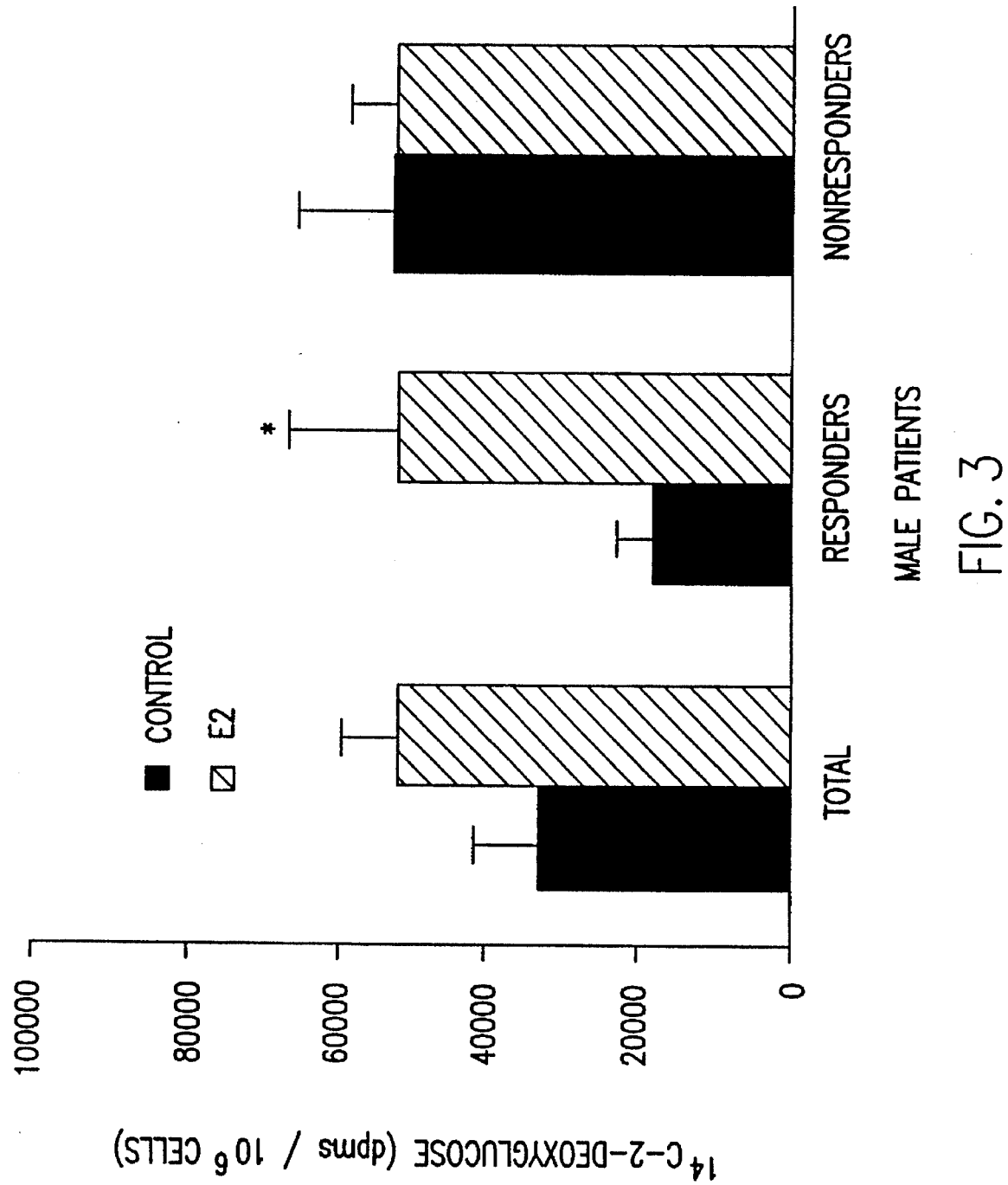
FIG. 3 shows the same as FIG. 2 but instead of females, males (n=9 patients) are the population under study.

Of the females, 9 of 12 subjects responded to $E_2\beta$ with a mean response of 230% (Table III, FIG. 2). Three of 12 female subjects failed to respond to the $E_2\beta$ exposure and exhibited only a 39% increase in $C^{14}$-2-DG uptake after 4 hours of exposure to estradiol (Table III). Male subjects were similarly analyzed for the significance of their response to $E_2\beta$. Five of 9 males tested showed a significant response to the steroid, while 4 subjects failed to respond (FIG. 3). The 5 responders showed a 188% increase in $C^{14}$-2-DG uptake in response to $E_2\beta$, while the nonresponders showed a −1% response to the steroid (Table III). Interestingly, the lack of response of the nonresponder males appeared to be related to the high initial values of $C^{14}$-2-DG uptake (FIG. 3).

Prognostic significance of in vitro glucose utilization tests.

Patient G was a 53 year old female who required estrogen replacement postmenopausally. She suffered from depression and hot flushes when not on estrogen and was taking Premarin at the time of the blood sample.

Patient K was a 64 year old woman who described the transition through the menopause as reasonably uneventful and did not respond to $E_2\beta$ replacement therapy postmenopausally.

As can be seen from FIG. 1, patient G had a relatively high level of responsiveness to estradiol whereas patient K had a small but lower level of responsiveness. Based on the predictive results of the test, patient G would have been recommended to use an estrogen replacement therapy whereas it is likely that patient K would not have been so advised.

Reproducibility of the test.

We assessed the ability of this in vitro method of determining estrogen responsiveness to reproducibly identify responders and nonresponders to $E_2\beta$ by repeating tests performed on responders and non-responders.

(a) Repeat testing: Two out of 2 nonresponders failed to respond upon re-testing. Also, all three responders in the first trial showed significant responses upon re-testing. Thus, for the patient population tested to date, the in vitro assessment of $C^{14}$-2-DG uptake give highly reproducible results.

Figure 4:
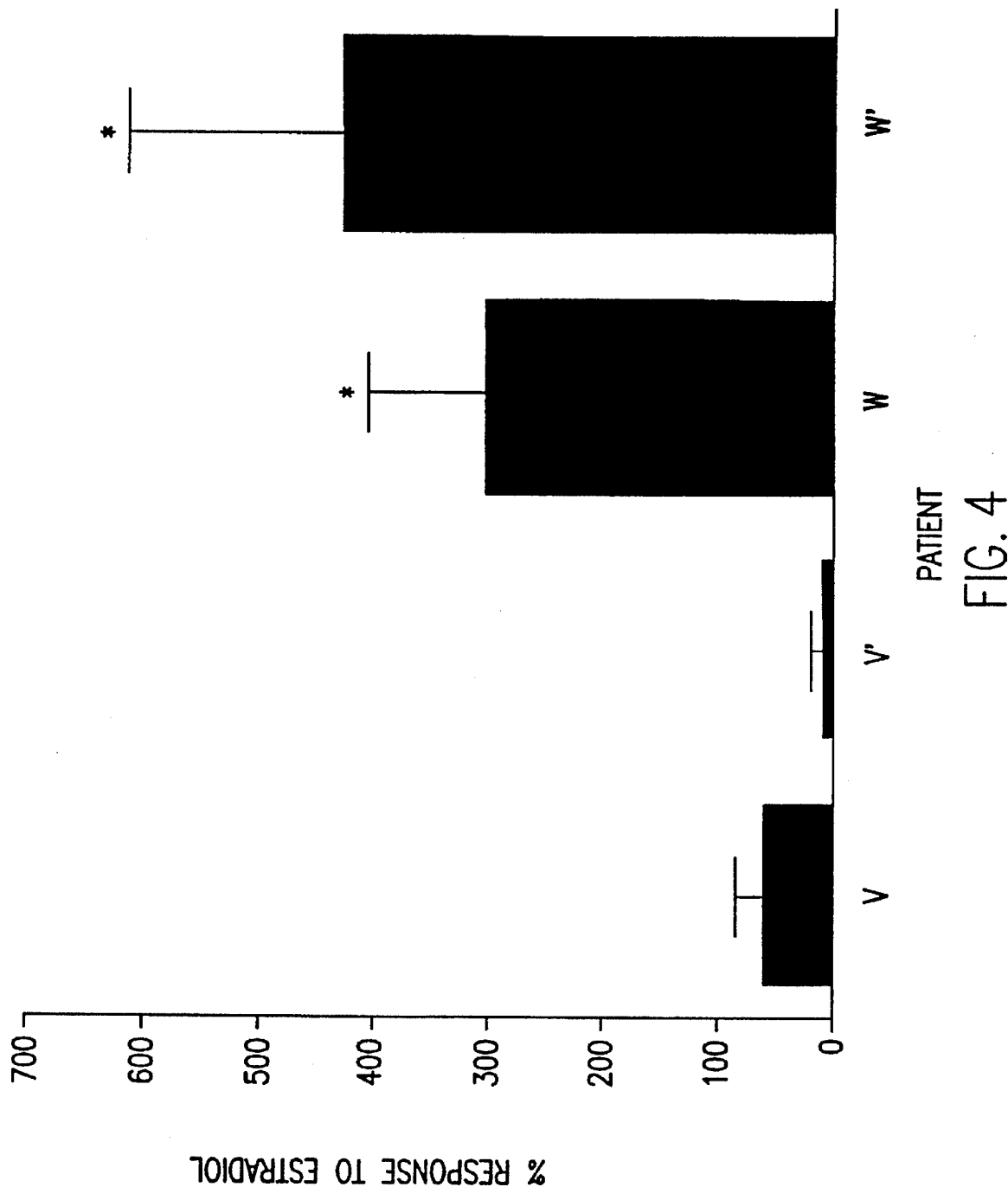
FIG. 4 shows an assessment of the effects of times of day on the $C^{14}$-2-deoxyglucose uptake response of erythrocytes to the in vitro exposure to $E_2\beta$. This study assessed the response of a non-responder (V and V') and a responder (W and W') when tested at 10:00 a.m. (V and W), after an overnight fast, and again at 2:00 p.m. (V' and W'), after a meal at 1.00 p.m. on the same day. Data for each patient are expressed as the percent response to $E_2\beta$ exposure (dpms $C^{14}$-2-deoxyglucose uptake in control media-exposed cells multiplied by 100).

(b) Impact of extraneous factors on testing: We assessed the effects of time of day and the recent ingestion of food on the $C^{14}$-2-DG uptake response of RBCs to $E_2\beta$ in vitro (FIG. 4). Two subjects, one nonresponder (Subject V) and one responder (Subject W) were assessed at 10:00 a.m. for their in vitro response to $E_2\beta$. Then they were feed a meal at 1:00 p.m. and re-assessed at 2:00 p.m. As shown in FIG. 4, neither the time of day, nor the recent consumption of a meal effected the response in the nonresponder or the responder.

(c) Correlation of questionnaire results detailing biological parameters characteristic of each patient with in vitro results. We reviewed the impact of questionnaire results on the magnitude of the in vitro $C^{14}$-2-DG uptake response of RBCs to $E_2\beta$ exposure. As shown in Table IV, when the Spearman's Rank Correlation Statistical Test was applied to the data, no correlations were found. As such, it appears that a variety of factors which might be expected to influence glucose uptake, such as age, body weight, stage of the menstrual cycle, plasma estradiol or glucose concentrations do not influence this in vitro response. Indeed, we have observed, as described above and depicted in FIG. 4, that time of day and recent food intake do not effect the in vitro response of RBCs to $E_2\beta$. As such, the test of estrogen responsiveness appears to be robust and resistant to compromising factors.

Example 1B

Assay of 7 Women Recruited as Post-Menopausal Subjects

Materials and Methods

Uptake of glucose by RBCs from human subjects.

A study was undertaken among seven women to establish the feasibility of using RBCs to monitor the effects of acute (4 h) exposure to $E_2\beta$ on the rate of glucose uptake. Freshly drawn, heparinized blood samples from healthy post-menopausal females were used. Subjects were recruited at random, questioned on the severity of their vasomotor symptomology, and a blood sample taken (under the auspices of the University of Florida IRB). RBC cells were immediately isolated from the plasma by centrifugation and the white cells were removed. The RBCs were washed three times with Krebs' phosphate buffer (pH=7.4). Finally, the cells were counted on a hematocytometer and resuspended in Krebs' phosphate buffer to obtain a concentration of approximately 5 million cells per ml. Then, 0.2 ml aliquots were placed in Eppendorf™ tubes. Samples were incubated at 37° C. and cells were pretreated for four hours with Krebs' phosphate buffer (control) or Krebs' phosphate buffer with 544 pg/ml of $E_2\beta$ at 37° C. Cells were pulsed with 100 µl of $^{14}$C-2-DG in 37° C. Krebs' phosphate buffer containing 0.5 µCi $^{14}$C-2-DG (specific activity 53.1 mCi/mmol, New England Nuclear, Boston, Mass.). After 20 minutes, $^{14}$C-2-DG was aspirated, cells were washed with phosphate buffered saline, vortexed, and centrifuged. Cells were solubilized with two 250 µl aliquots of 1% SDS (sodium dodecyl sulfate), five ml of Formula 989 scintillation cocktail was added, and samples were counted on a Beckman LS 5000 scintillation counter.

As depicted in Table V, four of seven subjects showed a significant increase in $^{14}$C-2-DG deoxyglucose uptake into RBCs in response to in vitro exposure to estradiol. In the three non-responders, the % response to estradiol was 98.9±5.5% (100%=uptake in control samples from the same subjects). By contrast, the 4 responders showed an estradiol effect on $^{14}$C-2-DG deoxyglucose uptake of 164±19.4% (p<0.05 vs. response in the non-responders).

Interestingly, the 3 non-responders failed to exhibit menopausal symptoms, including hot flushes, sleep disturbances, or emotionality. By contrast, the 4 responders demonstrated a marked increase in neurological symptoms related to the menopause. When a "Composite Neurological Score" (=number of hot flushes per day plus subjective rating of sleep disturbances [1 to 5 scale, with 5 being worst] plus subject rating of emotionality [1 to 5, with 5 being the worst]) was calculated, the three non-responders scored between 0 and 0.067, while the four responders scored between 5 and 21.

The data shows good agreement between the in vitro response of RBCs to estradiol and the symptomology of the subjects. While not wishing to be bound by theory, we propose that based on the results obtained in this study, symptomatic subjects may exhibit an estrogen-dependence of their GLUT1 transporter mechanism and as such require estrogen for the sufficient transport of glucose into the brain. By contrast, the non-symptomatic subjects may have an estrogen-independent GLUT1 transport and therefore do not require the ovarian hormone to maintain sufficient delivery of glucose to the brain.

EXAMPLE 2

Estrogens Regulate Glucose Uptake in Glial Cells

In Example 1, estrogen was demonstrated to affect glucose utilization by RBC. In this example, estrogen is demonstrated to affect glucose utilization in glioma cells.

Materials and Methods

Cell cultures.

$C_6$ glioma cell lines were obtained from American Type Culture Collection (Rockville, Md.). Culture conditions have been described previously (Keller et al., 1976, Kolbe et al., 1976). Cell cultures were grown to confluency in RPMI 1640 media (Sigma, St. Louis, Mo.) supplemented with 200 mM 1-glutamine, 100 IU/ml penicillin, 100 µg/ml streptomycin and 10% fetal bovine serum (FBS) (all reagents from Sigma Chemical Corporation, St. Louis, Mo.) in monolayers in plastic Falcon 25 cm$^2$ flasks (Fisher Scientific Inc., Orlando, Fla.) at 37° C. and under 5% $CO_2$ and 95% air. The media was changed three times a week. Cells were observed on a phase contrast microscope (Nikon Diaphot-300, Southern Micro Instruments, Orlando, Fla.) and were counted on a Neubauer hemacytometer (Fisher Scientific Inc., Orlando, Fla.). All experiments were performed in cells that were in passage number 3–9.

$E_2\beta$ effect on glucose uptake.

Forty eight hours before the measurement of glucose uptake, cells were backcultured, plated at 1 ml/well at a concentration of 1×10$^6$ cells/ml in 24 well plates and changed to fresh medium. Four hours prior to the C$^{14}$ evaluation, monolayers were washed with serum-free RPMI and wells were divided into treatment groups (one treatment group equals 6–12 wells) each well containing $E_2\beta$ (54 or 544 pg/ml) (Steraloids, Inc., Wilton, N.H.) or vehicle (Krebs Ringer Phosphate). Just prior to adding C$^{14}$-2-DG, cells were washed twice with 37° C. Krebs Ringer Phosphate (glucose free). Cells were then refed with 500 µl 37° C. Krebs' Ringer Phosphate containing 0.5 µCi C$^{14}$-2-DG (New England Nuclear, Boston, Mass. specific activity of 49.0–52.7 mCi/mmol in sterile aqueous solution). The linearity of glucose uptake was assessed over time. After 0, 2.5, 5, or 20 minutes of incubation at 37° C., 2-DG transport was terminated by aspirating radioactive medium, then washing cells twice rapidly with 1 µl ice cold phosphate buffered saline (PBS), pH 7.4 and solubilizing with 1% sodium dodecyl sulfate. Lyzates were placed in scintillation solution (New England Nuclear, Boston, Mass.) and were counted. Data were expressed as dpms/1×10$^6$ cells.

Results

Figure 5:
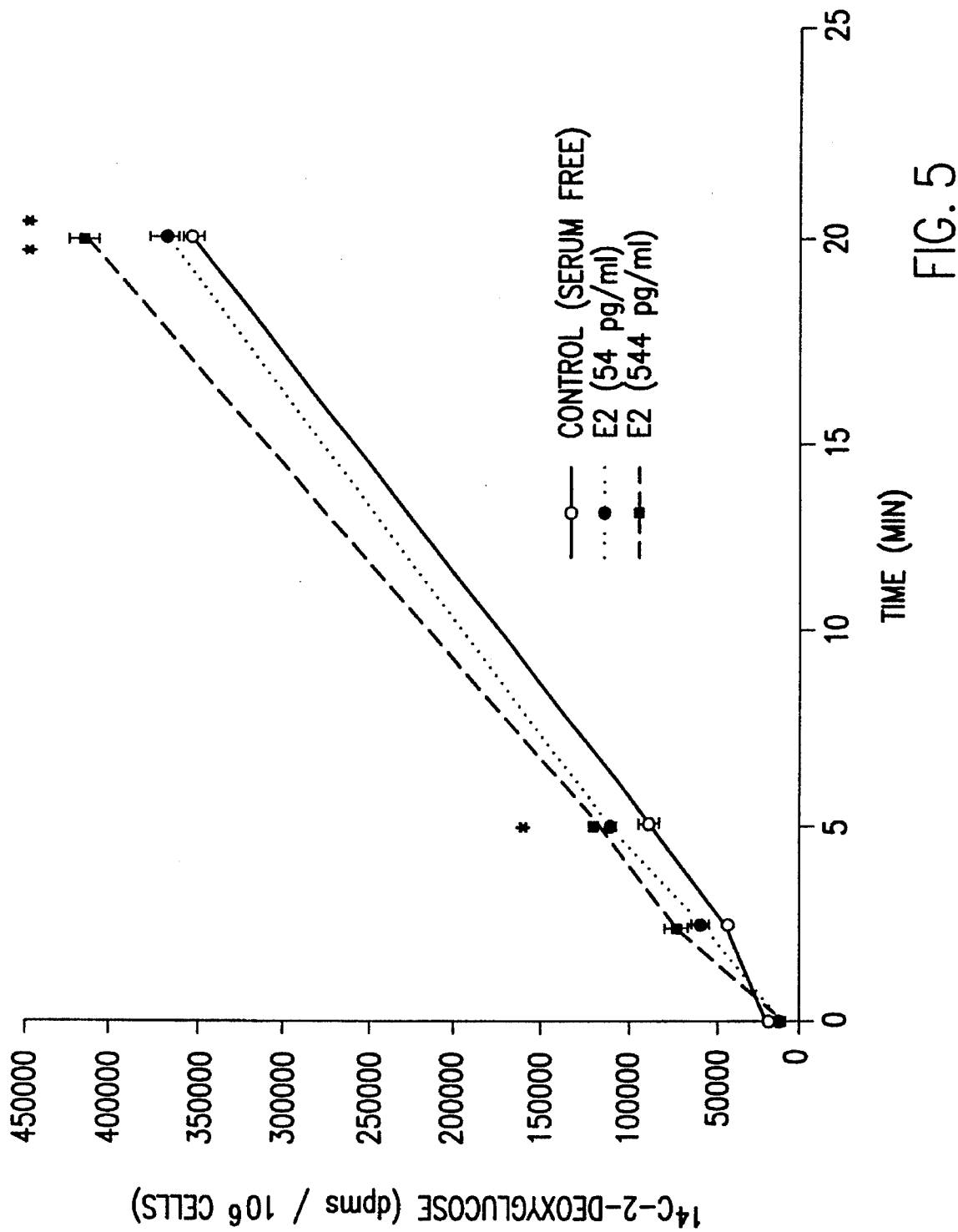
FIG. 5 shows the effect of the addition of $E_2\beta$ (54 pg/ml or 544 pg/ml) to serum-free media on the uptake of 2-DG in rat C6 glioma cells. * $p<0.05$ when compared to the serum-free group (544 pg/ml) ** $p<0.05$ when compared to the serum-free and $E_2\beta$ (54 pg/ml) group. Depicted are means+ sem. When sem bars are not shown, they are smaller than the symbols used to depict the mean value (n=6 wells/treatment/time point).

In $C_6$ cultures, uptake of 2-DG was linear for 20 minutes and the variance of the 2-DG uptake was low (FIG. 5). Both doses of $E_2\neq2$ (54 and 544 pg/ml, 4 hr $E_2\beta$ exposure) increased 2-DG uptake when compared to serum-free controls. The maximal increase in 2-DG uptake after 4 h $E_2\beta$ exposure was 30% for both doses tested, but there was a difference in the timing of this effect. The low $E_2\beta$ dose, 54 pg/ml, showed its maximal effect at 5 minutes whereas the higher $E_2\beta$ dose, 544 pg/ml, had its greatest effect on glucose uptake at 20 minutes.

The findings described in this example show that $E_2\beta$ significantly increases 2-DG uptake into $C_6$ cells. This finding is also correlated with the findings of Example 3 below in which $E_2\beta$ protects $C_6$ cells from the effects of sustained hypoglycemia.

EXAMPLE 3

Estrogens Protect Against the Cytotoxic Effects of Hypoglycemia

In this example, estrogen is shown to protect glioma cells ($C_6$ cells) from the cytotoxic effects of hypoglycemia.

Materials and Methods $C_6$ cells were plated in RPMI media with FBS at a concentration of 1×10$^6$ cells/ml in tissue culture flasks. Four hours prior to the onset of hypoglycemia, the maintenance media was discarded and monolayers were washed twice in the appropriate media. Cells were incubated for four hours at 37° C. in either serum-free RPMI media or serum-free media plus 544 pg/ml $E_2\beta$. Krebs' Ringer Phosphate was used to wash the monolayers twice before the addition of appropriate glucose treatment. RPMI medium contains 2 mg/ml glucose; flasks were divided into groups of 6 receiving either 100% glucose (2 mg/ml), 80% glucose (1.6 mg/ml), 60% glucose (1.2 mg/ml) or 0% glucose (buffer) with no steroid addition or supplemented with 544 pg/ml $E_2\beta$. All flasks were incubated for 20 hours and then evaluated for total, live, and dead cell number using trypan blue staining.

Results

Figure 6:
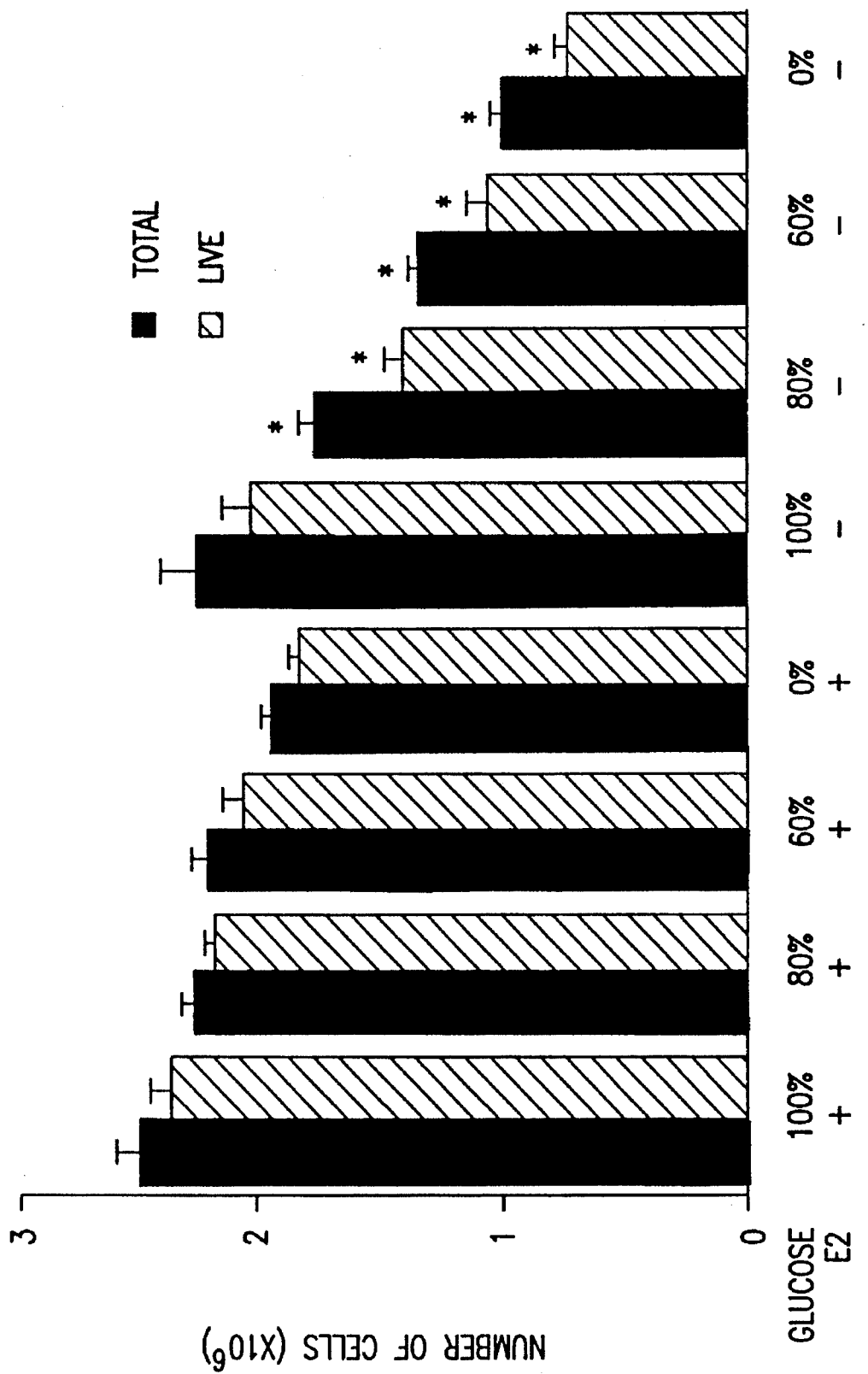
FIG. 6 shows the effect of the addition of $E_2\beta$ (544 pg/ml) to media on total and viable C6 glioma cells under varying conditions of hypoglycemia. * $p<0.05$ when compared to the appropriate $E_2\beta$-treated group (n=6 flasks/treatment).

Exposure of $C_6$ cells to hypoglycemic conditions caused a hypoglycemic dose-dependent reduction in both total and viable cell number (FIG. 6). Four hours of $E_2\beta$ exposure significantly improved both total and live cell numbers in response to 20 h of exposure to each of the hypoglycemic states (FIG. 6). The addition of $E_2\beta$ to serum-free media decreased the loss of total cells by 24% at 80% glucose; 38% at 60% glucose and 49% at 0% glucose. Similar protection of live cell numbers was observed at each of the reduced glucose concentrations with $E_2\beta$ increasing the number of viable cells by 35 to 60% when compared to serum-free cultures.

ANALYSIS OF DATA IN EXAMPLES 2 AND 3

All data are presented as mean±SEM after correcting for the dilution factor allowing the data to be expressed as the number of cells per ml. All experiments have been replicated at least twice. Hypoglycemia and glucose uptake data were analyzed by an analysis of variance followed by Scheffe's F test. The criterion for significance was $p<0.05$.

EXAMPLE 4

Estrogen Enhances Cerebral Glucose Uptake at Sites in the Brain

The effect of estradiol benzoate ($E_2\beta$) on cerebral glucose uptake in various brain regions which contain variable numbers of $E_2\beta$ receptors is described and the determination concerning increases in the amount of glucose transported into the brain in the presence of $E_2\beta$ is also described for a selected animal model.

Materials and Methods

Female rats were bilaterally ovariectomized to eliminate endogenous estrogens and two to three weeks later were implanted with an atrial cannula for the i.v. administration of $C^{14}$-2-deoxyglucose ($C^{14}$-2-DG) to unanesthetized rats. Animals were allowed four to five days to recover from the cannulation before the study was initiated.

On the day of the experiment, animals were randomized and assigned to groups which received either $E_2\beta$ in oil or oil alone (controls) administered subcutaneously at the dose and times described below. In our initial study, animals were treated with oil or $E_2\beta$ (10 µg/kg body weight) and were sacrificed at 2, 4, 8, 12 or 24 h. In an additional study, rats were treated with oil or $E_2\beta$ at doses of 1, 10 or 100 µg/kg body weight and were sacrificed 4 h later. Forty-five minutes prior to sacrifice, all rats received a single injection via the atrial cannulae of $C^{14}$-2-DG (25 µCi/ml saline/kg body weight; specific activity 49–53 mCi/mmol, New England Nuclear, Boston, Mass.).

Determination of brain uptake index.

To assess the effects of $E_2\beta$ on transport of glucose across the blood-brain barrier we used the technique of Oldendorf (Oldendorf, Brain Res. 24:37–46; 1970; and Am. J. Physiol. 221:1629–1638 (1971)). One µCi/ml of $C^{14}$-2-DG (specific activity 49–53mCi/mmol, New England Nuclear, Boston Mass.) and approximately five µCi/ml of $3H_2O$ (specific activity 1 mCi/ml, New England Nuclear, Boston, Mass.) were mixed with Krebs' Ringer Phosphate solution buffered to pH 7.4 with 10mM HEPES and injected into the carotid artery of female rats.

Fifteen seconds after injection, the animals were killed by decapitation, trunk blood was collected for later assay of serum $E_2\beta$ concentrations and the brain was removed from the cranium for dissection of the following regions: medial basal hypothalamus (MBH), preoptic area (POA), cortex, hippocampus, striatum, cerebellum and brainstem. The anterior pituitary (AP) was also isolated from the cranium. The dissection of brain tissues followed the methods of Glowinski and Iversen (Glowinski et al., J. Neurochem. 13:655–669 (1966)). Tissues were immediately weighed and placed in scintillation vials for processing. The mg weights (mean±SEM) of tissues used in these studies were: MBH= 13.4±1.3; POA=10.5±0.5; cortex=38.7±3; hippocampus= 27.7±1.7; striatum=24.3±2; cerebellum=32.5±1.9; brainstem=32.9±1.9 and AP=8.6±0.6.

During the procedure, peripheral plasma glucose values were in the normal range of 90–120 mg %.

Alternatively, half of the brain was dissected rostral to the midbrain and ipsilateral to the injection side, tissue passed through a 20 gauge needle and the sample subjected to routine digestion and then prepared for liquid scintillation counting as described above. An aliquot of original isotope mixture was obtained by recovering the residual mixture in the injection syringes. Both aliquot and tissue samples were then counted for $H^3$ and $C^{14}$ by routine liquid scintillation counting. Uptake by the Brain Uptake Index (BUI) was calculated after correcting for counting efficiency using the following equation for extraction (E):

$$E = \frac{C^{14} \text{ in brain tissue}/^3H \text{ in brain tissue}}{C^{14} \text{ in mixture}/3H \text{ in mixture}} \times 100$$

Statistical analysis.

Table VI provides a sample of data generated within one experiment. Evaluations of the time or dose effect of $E_2\beta$ on glucose uptake were done using a one way ANOVA. Post hoc comparisons were done with Dunnett's tests. These statistical analyses were performed on raw data (dpms $C^{14}$/mg tissue) by comparing the dpms for the $E_2\beta$-treated group with its control (oil) group at each dose and at each time point evaluated. For clarity of presentation, the raw data were then expressed as percent of mean control. The magnitude of the response of each $E_2\beta$-treated animal was determined by calculating the percentage increase of 2-DG uptake relative to the mean value of 2-DG uptake in the oil-treated control group. BUI data were analyzed by a one-tailed t-test for independent samples. Statistical difference was set at $p<0.05$ for all tests.

Results

The time course of the effects of a 10 µg/kg body weight dose of $E_2\beta$ on glucose uptake is shown in Table VI. Overall, $E_2\beta$ increased glucose uptake significantly in ovariectomized rats by 20 to 120% in 7 of 8 regions examined. However, the time at which a significant increase was observed varied among regions. For 5 of 8 regions, the POA, hippocampus, striatum, cerebellum and AP, the peak $E_2\beta$ effect was observed at 2 to 4 hours, while 2 regions showed peak effects at 12 hours (the MBH and cerebral cortex). Five regions showed a significant decline in glucose uptake at some time-point after an $E_2\beta$-induced increase. These regions were the POA, the hippocampus, the striatum, the cerebellum and the AP. No significant effect of $E_2\beta$ on brainstem glucose uptake was observed.

The dose-dependency of the $E_2\beta$ effect on brain glucose uptake at 4 hours post-$E_2\beta$ injection is shown in Table VII. The 1 µg/kg dose of $E_2\beta$ had no effect on brain glucose uptake. In contrast, the 10 µg/kg dose of $E_2\beta$ increased glucose uptake in 6 of 8 regions examined at the 4 h time point. Furthermore, only two regions exhibited increased glucose uptake at the 100 µg/kg dose of $E_2\beta$, the MBH and the POA. All other regions examined exhibited a reduced glucose uptake, with three regions, the striatum, the cerebellum and the brainstem, showing a significant reduction.

Serum $E_2$ concentrations were observed to increase in a dose-dependent manner 4 h post $E_2\beta$ injection. The 1 µg/kg $E_2\beta$ dose did not elevate serum $E_2\beta$ levels above those observed in ovariectomized rats, the 10 µg/kg $E_2\beta$ dose increased serum $E_2\beta$ levels into the physiological range, and the 100 µg/kg dose increased serum $E_2\beta$ levels, which were 12 to 30 times those seen during peak serum $E_2\beta$ concentrations on proestrus. Peak serum $E_2\beta$ levels were observed at 4 hours after administration of a 10 µg/kg dose of $E_2\beta$.

Our evaluation of BUI using the Oldendorf method indicates that 4 h of exposure to $E_2\beta$ increased the transport of glucose across the blood-brain barrier by about 40%. The 40% increase in BUI was accomplished by an $E_2\beta$-induced increase in $C^{14}$-2-DG extraction with no change in $^3H_2O$ extraction across the blood-brain barrier (Table VIII)

Although certain preferred embodiments of the present invention have been described, the spirit and scope of the invention is by no means restricted to what is described above. For example, a device for conducting the assay is desirable. Furthermore, although human subjects are specified, the test may also be applied to other mammals. The examples utilize one form of estrogen for administration to patients. Responsiveness to hormones other than those specified above and indeed responsiveness to any administered molecule may be evaluated in the assay of this invention for the applications as described and claimed herein (as described in. In addition, other means of measuring glucose uptake may be incorporated into an assay format to establish responsiveness of a human subject to hormone therapy.

TABLE I

CHARACTERISTICS OF PATIENT POPULATION USED FOR THE IN VITRO ASSESSMENT OF $C^{14}$-2-DEOXYGLUCOSE UPTAKE IN ERYTHROCYTES

|  | TOTAL | MALE | FEMALE |
|---|---|---|---|
| NUMBER | 21 | 9 | 12 |
| AGE (yr) | 38.0 ± 2.3 | 39.6 ± 3.0 | 36.8 ± 3.4 |
| RACE: |  |  |  |
| Caucasian | 19 | 9 | 10 |
| African | 1 | 0 | 1 |
| Asian | 1 | 0 | 1 |
| WEIGHT (kg) | 72.9 ± 2.9 | 81.2 ± 3.1 | 66.7 ± 3.6 |
| HEIGHT (m) | 1.71 ± 0.02 | 1.78 ± 0.02 | 1.65 ± 0.02 |
| WEIGHT/HEIGHT RATIO (kg/m) | 42.7 ± 1.6 | 45.6 ± 1.5 | 40.5 ± 2.4 |
| SMOKING STATUS | 7 | 2 | 5 |
| AFTER MEAL STATUS | 13 | 6 | 7 |

TABLE II

THE EFFECT OF $E_2\beta$ ON ERYTHROCYTE GLUCOSE UPTAKE IN THE PATIENT POPULATION

|  | $C^{14}$-2-DEOXYGLUCOSE (dpms/ 1 × 10$^6$ cells) | |
|---|---|---|
| PATIENTS | CONTROL (Krebs) | $E_2\beta$ (Krebs + $E_2\beta$) |
| TOTAL (n = 21) POPULATION | 28915 ± 5357 | 65641 ± 16951* |
| MALE (n = 9) | 32766 ± 8477 | 51070 ± 7959 |
| FEMALE (n = 12) | 26026 ± 7095 | 76570 ± 27985* |

Using a 1-way ANOVA to assess the three different populations under control (Kreb's) or #2 stimulated conditions there was no difference. However, using a 2-sample t-test for independent measures to evaluate the $E_2\beta$-effect, a significant (* p < 0.05) $E_2\beta$ induced glucose uptake in erythrocytes was observed both in the total population and in the female population.

TABLE III

THE EFFECT OF $E_2\beta$ ON ERYTHROCYTE GLUCOSE UPTAKE IN THE PATIENT POPULATION

|  | $C^{14}$-2-DEOXYGLUCOSE (dpms/ 1 × 10$^6$ cells) | | |
|---|---|---|---|
| PATIENTS | CONTROL (Krebs) | $E_2\beta$ (Krebs + $E_2\beta$) | % $E_2\beta$ RE-SPONSE |
| TOTAL (n = 21) POPULATION | 28915 ± 5357 | 65641 ± 16951* | 127% |
| MALE (n = 9) | 32766 ± 8477 | 51070 ± 7959 | 56% |
| Responders (n = 5) | 17716 ± 5445 | 50970 ± 14341* | 188% |
| Non-responders (n = 4) | 51578 ± 13016 | 51195 ± 6108 | −1 |
| FEMALE (n = 12) | 26026 ± 7095 | 76570 ± 27985* | 194% |
| Responders (n = 9) | 28148 ± 8072 | 93009 ± 37721** | 230% |
| Non-responders (n = 3) | 19662 ± 6161 | 27251 ± 10023 | 39% |

* $p < 0.05$ utilizing a 2-way t-test for independent samples.
**$p = 0.05$ utilizing a 2-way t-test for independent samples.

TABLE IV

CORRELATION BETWEEN IN VITRO ESTROGEN RESPONSIVENESS OF RBCs AND IN VIVO VARIABLES

| VARIABLE | SPEARMAN'S RANK CORRELATION COEFFICIENT |
|---|---|
| SEX | 0.173 |
| AGE (yr) | −0.294 |
| WEIGHT (kg) | −0.242 |
| HEIGHT (m) | −0.164 |
| BODY WEIGHT RATIO (kg/m) | −0.209 |
| STAGE IN MENSTRUAL CYCLE | 0.286 |
| PLASMA $E_2\beta$ (pg/ml) | −0.047 |
| SMOKING | 0.384 |
| PLASMA GLUCOSE (mg %) | −0.184 |
| PLASMA LACTATE (mg %) | 0.094 |

Using Spearman's rank correlation statistical test, there was no significant relationship between the $E_2\beta$-induced glucose uptake response in erythrocytes and any of the 10 variables evaluated.

TABLE V

EFFECTS OF IN VITRO EXPOSURE OF RBCs TO $E_2\beta$ ON $^{14}$C-2-DEOXYGLUCOSE UPTAKE IN SEVEN POST-MENOPAUSAL WOMEN

|  | Subject 1 | Subject 2 | Subject 3 | Subject 4 | Subject 5 | Subject 6 | Subject 7 |
|---|---|---|---|---|---|---|---|
| % Response to Estradiol | 85 ± 2 | 103 ± 3 | 154 ± 8* | 137 ± 6* | 108 ± 5 | 135 ± 24* | 230 ± 40* |
| # Flushes per day | 0 | 0.067 | 2 | 5.5 | 0 | 0.05 | 12 |
| Vaginal Dryness Index | 0 | 0 | 3 | 10 | N/A | 0 | 8 |
| Sleep Disturbance | 0 | 0 | 5 | 5 | 0 | 5 | 4 |

TABLE V-continued

EFFECTS OF IN VITRO EXPOSURE OF RBCs TO $E_2\beta$ ON $^{14}C$-2-DEOXYGLUCOSE UPTAKE IN SEVEN POST-MENOPAUSAL WOMEN

| | Subject 1 | Subject 2 | Subject 3 | Subject 4 | Subject 5 | Subject 6 | Subject 7 |
|---|---|---|---|---|---|---|---|
| Emotionality | 0 | 0 | 1 | 5 | 0 | 0 | 5 |
| Composite Neurological Score | 0 | 0.067 | 8 | 15.5 | 0 | 5.05 | 21 |

% Response to Estradiol: Depicts the dpm of $^{14}C$-2-DG taken up into 4 to 5 replicates of RBCs exposed to $E_2\beta$ divided by dpms $^{14}C$-2-DG taken up into 4 to 5 replicates of RBCs exposed to control media multiplied by 100.
\# Hot Flushes Per Day: Was determined from a survey conducted at the time of the blood sampling.
Vaginal Dryness Index: Was determined from the number of painful intercourses of the last 10 occurrences.
Sleep Disturbance: Subjects were asked to rate the extent of their problem with spontaneous awakening during the night (on a 1 to 5 scale, with 5 being the worst).
Emotionality: Was scored based upon the subjective assessment of unexplaned crying episodes (on a 1 to 5 scale, with 5 being the worst).
Composite Neurological Score: Number of hot flushes per day plus subjective rating of sleep disturbances plus subjective rating of emotionality.
*Indicates a significant response to $E_2\beta$ ($p < 0.05$) as analyzed by a 2-way t-test for independent samples of 4 to 5 samples in each of the control and E2 exposed cells.

TABLE VI

ESTROGEN AND GLUCOSE UPTAKE IN VARIOUS BRAIN REGIONS TIME COURSE EFFECTS OF A 10 μg DOSE OF $E_2B$ ON 4 HOUR GLUCOSE UPTAKE IN A VARIETY OF BRAIN REGIONS AND THE ANTERIOR PITUITARY GLAND

| BRAIN REGIONS | TIME | | | | |
|---|---|---|---|---|---|
| | 2 HR | 4 HR | 8 HR | 12 HR | 24 HR |
| Medial Basal Hypothalamus | 116 ± 15 | 154 ± 24* | 110 ± 20 | 265 ± 15* | 108 ± 7 |
| Preoptic Area | 132 ± 22* | 221 ± 62* | 80 ± 11 | 67 ± 4* | 98 ± 15 |
| Cerebral Cortex | 76 ± 10* | 98 ± 9 | 120 ± 17 | 215 ± 28* | 100 ± 7 |
| Hippocampus | 132 ± 18* | 125 ± 14* | 71 ± 10* | 88 ± 6 | 93 ± 5 |
| Striatum | 94 ± 30 | 140 ± 17* | 62 ± 9* | 88 ± 6 | 103 ± 7 |
| Cerebellum | 121 ± 29 | 120 ± 14* | 73 ± 9* | 110 ± 62 | 107 ± 9 |
| Brainstem | 111 ± 24 | 90 ± 7 | 70 ± 6 | 118 ± 12 | 94 ± 11 |
| Anterior Pituitary | 95 ± 10 | 220 ± 39* | 142 ± 28 | 66 ± 6* | 125 ± 7* |

* $p < 0.05$ versus control value within a brain region. Evaluation of the time effect was made with a one-way ANOVA. After analysis and for clarity of presentation data was transformed to percent of mean control.

TABLE VII

ESTROGEN AND GLUCOSE UPTAKE IN VARIOUS BRAIN REGION DOSE-DEPENDENT EFFECTS OF 4 HR $E_2B$ EXPOSURE ON GLUCOSE UPTAKE IN A VARIETY OF BRAIN REGIONS AND THE ANTERIOR PITUITARY GLAND

| BRAIN REGIONS | $E_2B$ DOSE | | |
|---|---|---|---|
| | 1 μg/Kg | 10 μg/Kg | 100 μg/Kg |
| Medial Basal Hypothalamus | 110 ± 23 | 154 ± 24* | 192 ± 28* |
| Preoptic Area | 98 ± 45 | 221 ± 62* | 155 ± 47* |
| Cerebral Cortex | 95 ± 27 | 98 ± 9 | 87 ± 11 |
| Hippocampus | 90 ± 19 | 125 ± 14* | 87 ± 12 |
| Striatum | 111 ± 29 | 140 ± 17* | 74 ± 8* |
| Cerebellum | 112 ± 20 | 120 ± 14* | 57 ± 11* |
| Brainstem | 116 ± 22 | 90 ± 7 | 47 ± 16 |
| Anterior Pituitary | 112 ± 32 | 220 ± 39* | 64 ± 25 |

TABLE VII-continued

ESTROGEN AND GLUCOSE UPTAKE IN VARIOUS
BRAIN REGION DOSE-DEPENDENT EFFECTS
OF 4 HR $E_2B$ EXPOSURE ON GLUCOSE UPTAKE
IN A VARIETY OF BRAIN REGIONS AND
THE ANTERIOR PITUITARY GLAND

| BRAIN | $E_2B$ DOSE | | |
|---|---|---|---|
| REGIONS | 1 μg/Kg | 10 μg/Kg | 100 μg/Kg |

* $p < 0.05$ versus control value. Evaluation of the dose effect was accomplished with a one-way ANOVA. Post hoc comparisons were done with a Dunnett's test. After analysis and for clarity of presentation data was transformed to percent of mean control.

TABLE VIII

ESTROGEN AND GLUCOSE UPTAKE IN
VARIOUS BRAIN REGIONS
Effect of $E_2B$ on the extraction of
$c^{14}$-2-deoxyglucose and $^3H_2O$ in the brain

| GROUP | $E_{2DG}$ | $E_{3H2O}$ |
|---|---|---|
| Oil | 0.0803 ± 0.011 | 0.1318 ± 0.943 |
| $E_2B$ | 0.1208 ± 0.013* | 0.1486 ± 0.313 |

* $p < 0.05$ when compared to oil control. Analyzed with a t-test for independent samples; n = 7, mean ± sem.

We claim:

1. A method for diagnosing responsiveness of a living human subject to an estrogen compound, comprising:
   (i) obtaining an ex vivo cell sample from the subject;
   (ii) exposing a first aliquot of the sample to the estrogen compound and glucose;
   (iii) exposing a comparable second aliquot of the sample to glucose only;
   (iv) measuring the amount of the glucose utilized by the first and second aliquots of steps (ii) and (iii) to obtain first and second measurements, respectively; and
   (v) correlating the first and second measurements obtained in step (iv), whereas when the first measurement is a greater value than the second measurement, the subject is responsive to the estrogen compound.

2. A method according to claim 1, wherein the hormone is estrogen.

3. A method according to claim 1, wherein step (iv) includes the step of measuring transmembrane glucose transport.

4. A method according to claim 1, wherein steps (ii) and (iii) further include the step of placing the aliquots in a reaction chamber for performing step (iv) in vitro.

5. A method according to claim 4, wherein the step (ii) further comprises the steps of:
   (a) incubating the aliquot with a buffer containing the estrogen compound in a reaction mixture for an effective time period, the effective time period being sufficient to permit subsequent enhancement of the uptake of glucose in the presence of the estrogen compound;
   (b) adding labelled glucose to the reaction mixture;
   (c) separating the sample from the reaction mixture; and
   (d) measuring the amount of labelled glucose in the sample.

6. A method according to claim 5, wherein the labelled glucose of step (b) is radioactive glucose.

7. A method according to claim 6, wherein the labelled glucose is $C^{14}$-2-deoxyglucose.

8. A method according to claim 1, wherein the sample is a body fluid.

9. A method according to claim 8, wherein the body fluid is selected from the group consisting of blood and urine.

10. A method according to claim 1, wherein the sample is a body tissue.

11. A method according to claim 10, wherein the body tissue is selected from the group consisting of red blood cells, white blood cells, and skin.

12. A method according to claim 11, wherein the body tissue is red blood cells.

* * * * *